(12) United States Patent
Öhman et al.

(10) Patent No.: US 7,610,087 B2
(45) Date of Patent: Oct. 27, 2009

(54) IMPLANTABLE CARDIOVERTER DEFIBRILLATOR WITH AUTOMATIC SWITCHING TO A PRE-SET PACING MODE FOLLOWING DELIVERY OF A SHOCK

(75) Inventors: Magnus Öhman, Hässelby (SE); Berit Larsson, Danderyd (SE)

(73) Assignee: St. Jude Medical Ab, Jarfalla (SE)

( * ) Notice: Subject to any disclaimer, the term of this patent is extended or adjusted under 35 U.S.C. 154(b) by 408 days.

(21) Appl. No.: 10/529,430

(22) PCT Filed: Aug. 19, 2003

(86) PCT No.: PCT/SE03/01297

§ 371 (c)(1),
(2), (4) Date: Nov. 2, 2005

(87) PCT Pub. No.: WO2004/028628

PCT Pub. Date: Apr. 8, 2004

(65) Prior Publication Data

US 2006/0155335 A1    Jul. 13, 2006

(30) Foreign Application Priority Data

Sep. 27, 2002    (SE) .................................... 0202881

(51) Int. Cl.
*A61N 1/365*    (2006.01)

(52) U.S. Cl. ............................................. 607/4; 607/28
(58) Field of Classification Search ...................... 607/4, 607/5, 28, 29
See application file for complete search history.

(56) References Cited

U.S. PATENT DOCUMENTS

| 4,869,252 | A | | 9/1989 | Gilli |
| 4,895,151 | A | * | 1/1990 | Grevis et al. ................... 607/4 |
| 6,157,859 | A | | 12/2000 | Alt |
| 6,327,498 | B1 | | 12/2001 | Kroll |
| 6,430,441 | B1 | * | 8/2002 | Levine ........................ 607/28 |
| 6,813,516 | B2 | * | 11/2004 | Ujhelyi et al. ................. 607/4 |

FOREIGN PATENT DOCUMENTS

WO    WO 99/65566    12/1999

* cited by examiner

*Primary Examiner*—George R Evanisko
*Assistant Examiner*—Amanda Patton
(74) *Attorney, Agent, or Firm*—Schiff Hardin LLP

(57) ABSTRACT

An implantable cardiac stimulator, such as a cardioverter defibrillator, is operable in an autocapture mode. Following the delivery of a defibrillation or cardioversion shock, the stimulator switches from the autocapture mode to a post-shock mode, in which predetermined pacing pulse parameter settings are used for the delivery of pacing pulses. Following the expiration of a predetermined time interval, which may be extendable, the stimulator switches back to the autocapture mode.

14 Claims, 3 Drawing Sheets

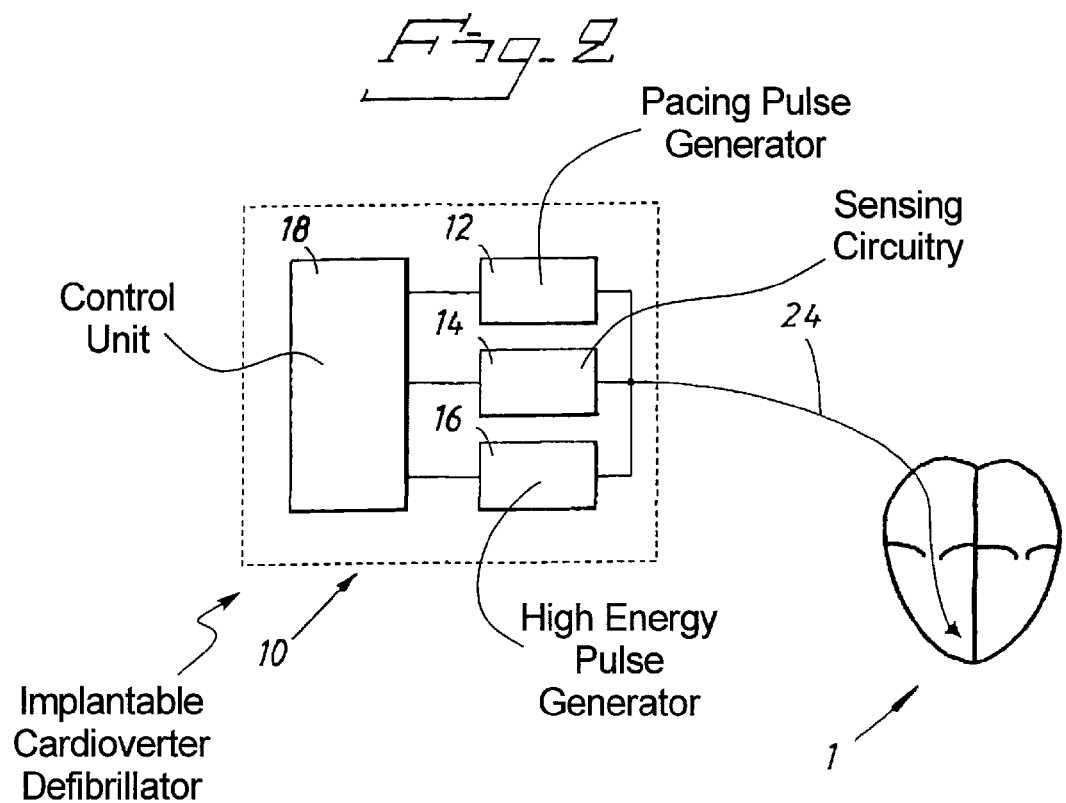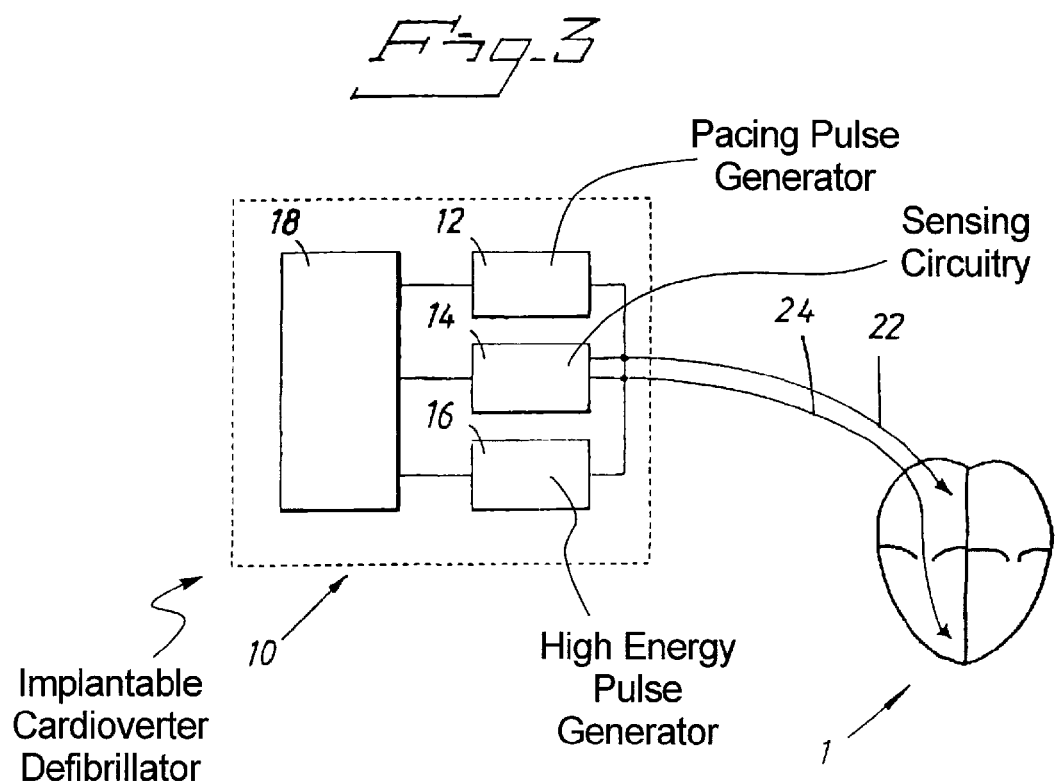

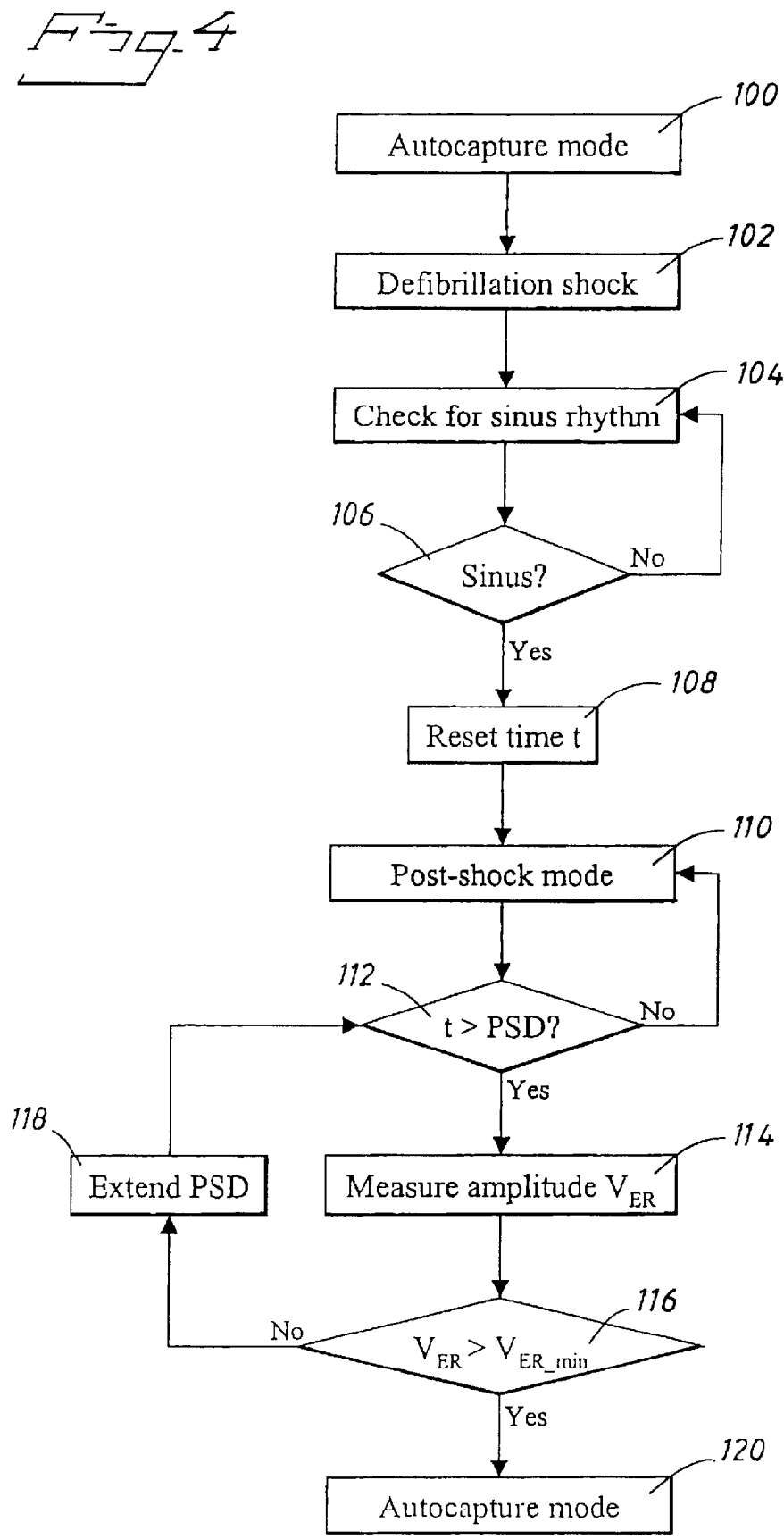

IMPLANTABLE CARDIOVERTER DEFIBRILLATOR WITH AUTOMATIC SWITCHING TO A PRE-SET PACING MODE FOLLOWING DELIVERY OF A SHOCK

BACKGROUND OF THE INVENTION

1. Field of the Invention

The present invention generally relates to the field of implantable cardioverter defibrillators. More specifically, the invention relates to an implantable cardioverter defibrillator (ICD) of the type including a system for automatic capture threshold determination.

2. Description of the Prior Art

Heart defibrillation is currently performed by the discharge of a powerful voltage pulse between two electrodes. The electrodes are placed so the discharge takes place over the heart or a large part thereof. The energy in a pulse amounts typically from a few joules up to a few dozen joules.

In order to reduce pacing energy consumption and increase longevity, methods for automatic capture threshold determination, or automatic regulation of pacing pulse settings, may be provided in cardiac stimulators for maintaining the energy of the stimulation pulses at a level just about what is needed to effectuate capture. One such method is known as the AutoCapture™ Pacing System of the type described in PCT Application WO 99/65566. Longevity is increased because automatic capture detection allows pacing at lower energies without compromising patient safety. It is also known to provide automatic capture pacing in an ICD system, see e.g. U.S. Pat. No. 6,327,498.

The autocapture functionality of the AutoCapture™ Pacing System automatically adapts the stimulation output to the minimal energy required to capture the heart. After each single delivered pacing stimulus, capture is verified. The verification is based on detection of the Evoked Response (ER), which is defined as the electrical response of the myocardium to a pacing stimulus. During a time window after an emitted pacing pulse, sensing circuitry of the heart stimulator looks for an evoked response. If an evoked response is not detected during the detection window, the heart stimulator interprets this as loss of capture and a back-up pulse of higher energy is emitted at the end of the detection window. Conversely, if an evoked response is detected capture is verified.

If two consecutive losses occur, then a threshold search will be performed in order to evaluate whether the pacing threshold has changed. If necessary, the pacing pulse settings will be adjusted such that subsequent pacing pulses will have a higher energy content as compared to the energy content of the two consecutive pulses that did not effect an evoked response. The process of changing the energy content in the pacing pulses is referred to as a threshold search. In this process, the energy content in the pacing pulses is adjusted in steps and capture is verified for each pacing pulse. After the threshold has been determined, a working margin is added to the measured threshold in order to determine the new pacing pulse settings following the threshold search. This working margin is typically in the order of 0.3 V.

The above discussed threshold search is caused by an increased threshold and will be executed immediately when two consecutive losses of capture has been detected. If the pacing threshold is stable for a longer period of time and no sudden changes occur, i.e. there is no consecutive losses of capture, then threshold searches will be initiated by a timer at regular intervals. These intervals are typically in the order of eight hours. This will allow for the pulse generator to adapt to threshold changes regardless of whether the threshold increases or decreases.

The large energy required in a defibrillation shock, e.g. an ICD shock, has shortcomings as regards the longevity of an ICD device. Furthermore, the powerful energy discharge in the ICD shock has adverse effects on the organism. For instance, it is known that the pacing or capture threshold is increased immediately following a defibrillation shock. Furthermore, the length of the depolarization phase may also be affected, as well as the length of the refractory period of the myocardium.

Thus, the results of automatic capture threshold detection, below simply referred to as autocapture, immediately following an ICD shock may differ considerably from the results of autocapture provided when the myocardium is not affected by a recent ICD shock, which may have an adverse effect on the accuracy of the autocapture measurements. For instance, autocapture measurements immediately following the delivery of a shock may result in a higher pacing threshold. The resulting higher pacing output will be used until the next threshold search is initiated by the timer. Furthermore, polarization from the pacing electrode may become modified immediately following the delivery of a shock. This can result in changes in the sensing signal used for detecting capture following a shock.

SUMMARY OF THE INVENTION

An object of the present invention is to provide an implantable cardioverter defibrillator in which the above-described drawbacks are reduced or eliminated.

The above object is achieved in accordance with the present invention in an implantable cardiac stimulator, such as a cardioverter defibrillator, having a pulse generator adapted for delivering pacing pulses to at least one chamber of a heart, a defibrillation unit adapted for delivering at least one of cardioversion shocks or defibrillation shocks to at least one chamber of the heart, sensing circuit for sensing intrinsic cardiac activity as well as cardiac activity resulting from capture following a delivered pacing pulse, a control unit for controlling the timing and energy of the pacing pulses and the cardioversion and/or defibrillation shocks, respectively, the control unit operating said pulse generator in a first operating mode including an autocapture mode, and a second operating mode for delivering pacing pulses according to predetermined pacing pulse settings, and wherein the control unit automatically switches from said first operating to said second operating mode following delivery of a cardioversion shock or a defibrillation shock.

Although it is preferable that the pulse generator be capable of delivering both cardioversion shocks and defibrillation shocks, respectively under appropriate conditions, the invention is equally applicable if the pulse generator is capable of delivering only cardioversion shocks or is capable of delivering only defibrillation shocks. Thus, the pulse generator need only be capable of generating at least one of a cardioversion shock or a defibrillation shock.

For the purposes of this application, it should be noted that there are a number of different methods for providing automatic capture detection, or automatic pacing pulse settings, known in the art, apart from the one described above. Autocapture mode of operation includes the following elements: a) detection of whether a delivered stimulation pulse has captured the heart or not, b) delivery of a back-up pacing pulse within a short period following a pacing pulse that did not capture the heart, and c) ability to determine the pacing threshold. The term "autocapture" referred to in the following relates to all such methods providing elements a-c mentioned above. In other words, the present invention is not restricted to an ICD having the particular autocapture functionality described above.

Thus, the present invention is based on providing an ICD having autocapture functionality with the ability to switch from an autocapture mode of operation to a post-shock mode of operation with predetermined pacing pulse settings following the delivery of a cardio-version or defibrillation shock. In other words, the autocapture mode of operation is paused following the delivery of a cardioversion or defibrillation shock. This will result in elimination of any adverse effects that may occur if autocapture is enabled immediately following a shock.

According to the present invention, the ICD is arranged to enter a post-shock operating mode following the delivery of a cardioversion or defibrillation shock, in the continuing simply referred to as the delivery of a shock. In the post-shock operating mode, the ICD utilizes predetermined parameter settings for the pacing or stimulating pulses.

In a first example, these settings can be programmed by the surgeon in connection with the implantation surgery, and thus preferably be based on capture threshold measurements conducted in connection with said surgery.

In a second example, the ICD could utilize predetermined pacing pulse settings that were programmed in connection with the manufacture or assembly of the ICD, i.e. before delivery of the ICD to the hospital where the implantation is to take place.

In a third example, the parameters of the predetermined pacing pulse settings could be programmed or adjusted after implantation and be based on pacing events measured during the every-day use of the ICD and stored in the ICD for later evaluation. Any combination of these examples is also conceivable without departing from the scope of the invention. In other words, the term "predetermined pacing pulse parameters" should be interpreted as being predetermined at the delivery of the shock.

According to preferred embodiments of the invention, the ICD is arranged to enter the post-shock operating mode first after the detection of sinus rhythm following the delivery of a shock.

Furthermore, the ICD returns from the post-shock operating mode to the autocapture mode following a certain time interval, below referred to as post-shock duration. According to exemplary embodiments of the invention, the post-shock duration is preprogrammed. Preferably, the post-shock duration is in the range of 1-15 minutes, more preferably in the range of 5-10 minutes. Following the expiry of the preprogrammed post-shock duration, the ICD is arranged to automatically return to the autocapture operating mode.

According to further embodiments of the invention, the time interval during which the ICD is operating in the post-shock operating mode may be extendable. For example, before the first predetermined time interval following a shock has expired, the ICD performs measurements of selected cardiac parameters and evaluates whether the time interval is to be extended.

Preferably, if the post-shock duration is indeed extended, the ICD repeats the measurement prior to the expiry of the thus extended post-shock duration, and to evaluate whether the extended post-shock duration should be extended even further. This may be repeated until the evaluation indicates that the post-shock duration shall not be further extended, or until the number of extensions, or the accumulated post-shock duration time, reaches a predetermined maximum post-shock duration limit. In the earlier case, the ICD returns to the autocapture operating mode following the expiration of the present time interval. However, in the latter case, the ICD could be returned to the autocapture operating mode, or maintain the post-shock operating mode until the ICD has been evaluated and, possibly, re-programmed by a physician during a follow-up.

According to one exemplary embodiment, the cardiac parameters include the amplitude of a heart activity signal measured by sensing circuitry of the ICD, e.g. the evoked response signal. Then, if the amplitude of the measured signal for instance exceeds or is less than a predetermined threshold value, the time interval is extended, preferably by a preprogrammed extension interval. Said cardiac parameters could also include the morphology or the polarization of the evoked response signal. For instance, the cardiac signal amplitude and morphology should not deviate too much from the cardiac signal amplitude and morphology before the delivery of a shock. Likewise, the polarization of the evoked response signal following a shock should be close to the polarization of the evoked response signal preceding the shock.

Preferably, the cardiac parameters are continuously monitored and stored, such that the measured parameters following a shock may be compared to the values of said parameters prior to the delivery of a shock. If the difference between the pre-shock and the post-shock parameters exceeds a predetermined threshold value, then the time interval may be extended.

In further embodiments of the invention, the duration of said preprogrammed extension interval is fixed, and preferably in the range of 2-15 minutes, more preferably in the range of 5-10 minutes. According to alternative embodiments of the invention, said extension interval, although preprogrammed, may be varied. As an example, a first extension interval could be in the range of 2-5 minutes, a second in the range of 3-8 minutes, a third in the range of 5-15 minutes, a fourth in the range of 10-30 minutes, etc. Thus, the first extension interval, or initial post-shock duration, can be made very short in order for the ICD to return to the autocapture mode of operation as quickly as possible, while simultaneously not having to repeat the measurements and evaluations more often than necessary. In this embodiment, the initial post-shock duration immediately following a delivered shock is preferably short, for example in the range of 1-5 minutes.

The pacing parameters that may be adjusted to predetermined pacing pulse settings when the ICD switches to a post-shock operating mode can for example include the base rate, the pacing pulse amplitude, the pacing pulse width, and the P/R-wave sensitivity. The pacing parameters could relate to either ventricular or atrial pacing pulses, or to both ventricular and atrial pacing pulses.

In further embodiments of the present invention, and without departing from the scope of the present invention, the ICD may be arranged for terminating a ventricular or an atrial arrhythmia or fibrillation, respectively, or both. Furthermore, the ICD may be arranged for delivering ventricular or atrial pacing pulses, respectively, or both. Also, the autocapture functionality referred to throughout this application may be applied to atrial pacing pulses, as well as to ventricular pacing pulses. According to an exemplary embodiment of the present invention, the ICD utilizes a single ventricular lead for delivering both defibrillation and cardioversion shocks to a ventricle of the heart, as well as for delivering the ventricular pacing pulses. Such an implantable lead is disclosed in U.S. Pat. No. 6,327,498, which is incorporated herein by reference in its entirety. This configuration also enables autocapture detection using one and the same lead.

According to other exemplary embodiments, the defibrillation and cardioversion shocks may be delivered through one lead, and the pacing pulses may be delivered through another lead, either ventricular or atrial. Then, the lead for pacing is preferably also used for sensing capture.

As understood by those skilled in the art, any defibrillation or cardioversion shock sequence may be used without departing from the scope of the present invention. For instance, the cardioversion may be in accordance with a stepped cardioversion algorithm, such as shown in U.S. Pat. No. 5,620,469. Another example can be found in European Application 588 125, which discloses an apparatus for defibrillating a human heart using a sequence of combined pacing pulses and defibrillation shocks.

DESCRIPTION OF THE DRAWINGS

FIGS. 2 and 3 are schematic illustrations of an ICD according to alternative embodiments of the present invention.

FIG. 4 is a flowchart illustrating the operation of the ICD according to an embodiment of the present invention following the delivery of a cardioversion or defibrillation shock.

DESCRIPTION OF THE PREFERRED EMBODIMENTS

Figure 1:
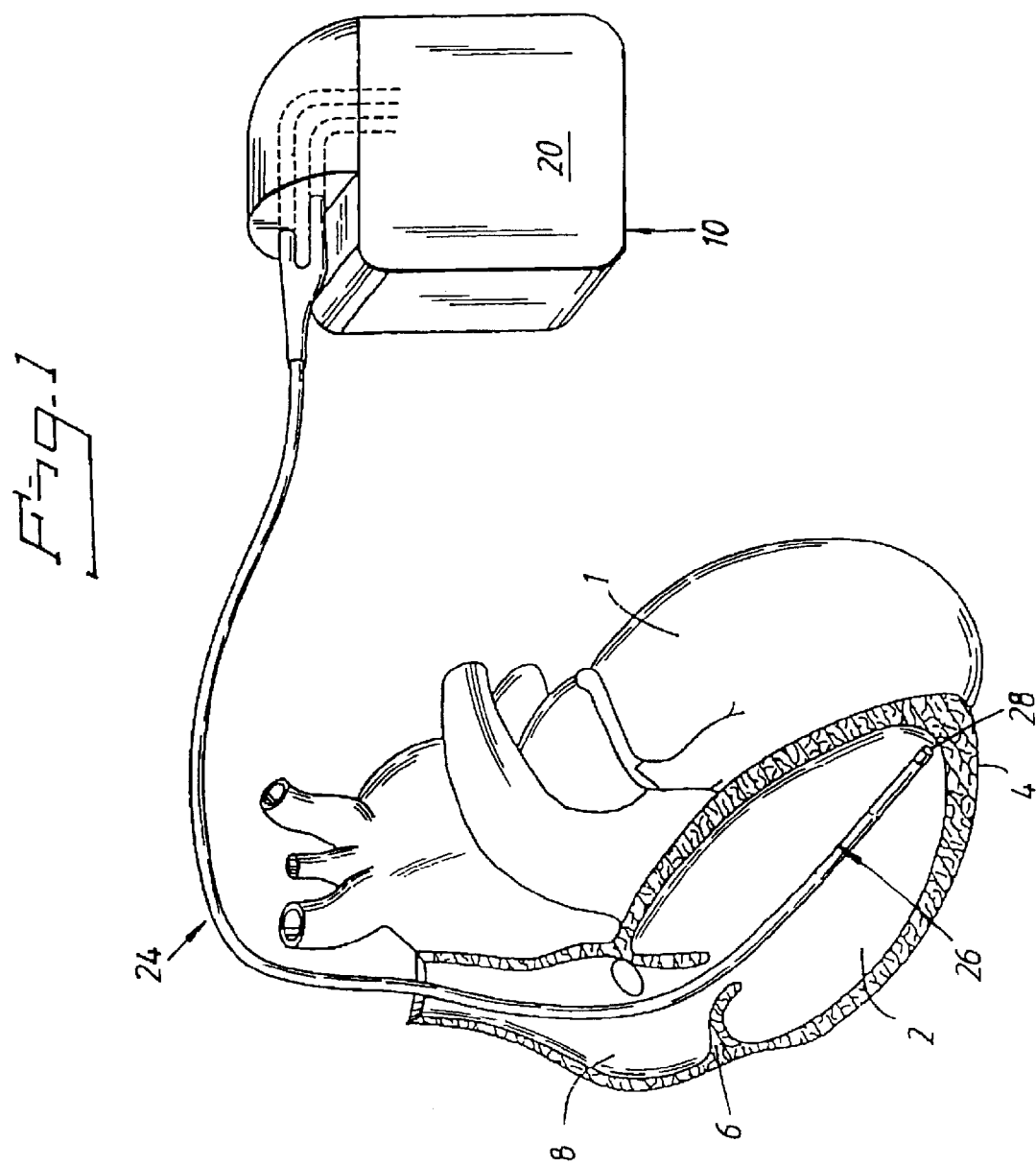
FIG. 1 is a diagrammatic, perspective view of an ICD system according to the present invention.

Referring first to FIGS. 1 and 2, a first embodiment of an implantable defibrillation system of the present invention is generally shown in the form of an implantable cardioverter defibrillator (ICD) 10, typically subcutaneously implanted between the skin and the ribs of the patient. An implantable, ventricular ICD lead system 24 is passed through a vein into the right ventricle 2 of a heart 1. The distal end of the lead system 24 has a tip electrode 26 contacting the interior of the ventricle, preferably at its apex 4.

According to the described embodiment, an elongated, annular shocking coil electrode 26, also referred to as a ring electrode, is spaced at a distance of about 1.5-3.0 cm from the tip electrode 28. The shocking coil extends in a direction towards the region of the tricuspid valve 6 between the right atrium 8 and the right ventricle 2 and typically has a length of about 2-6 cm.

Each of these electrodes is connected, via the ventricular lead 24, to the circuitry contained in the ICD 10. The metallic enclosure or "can" of the ICD 10 also forms an electrode surface 20.

A variety of lead configurations can be used in order to pace the heart, to sense the intrinsic depolarizations of the heart, and to deliver defibrillation or cardioversion shocks to the heart. However, according to a first embodiment of the invention, there is disclosed a configuration where ventricular pacing and sensing are accomplished using the tip electrode 28 and the shocking coil electrode 26 of the ventricular lead 24. Defibrillation is delivered using the shocking coil electrode 26 and the can electrode 20. Thus, the ventricular lead 24 may be utilized both for ventricular pacing and as a defibrillator lead. According to a second embodiment, however, both ventricular pacing and defibrillation is delivered using the shocking coil electrode 26 and the can electrode 20.

According to a further embodiment, the lead comprises two ring electrodes as well as a tip electrode, for instance as described in the above-mentioned U.S. Pat. No. 6,327,498, which is incorporated herein by reference. Then, defibrillation is delivered using one ring electrode and the can, and pacing is delivered using the other ring electrode and the can.

The can 20 of the ICD 10, as mentioned above, which also acts as an electrode. The can 20 contains a pacing pulse generator 12 for delivering pacing pulses, sensing circuitry 14 for detecting ventricular evoked response or capture, and a high energy pulse generator 16 for delivering cardioversion and/or defibrillation shocks. The ventricular lead 24 is connected to each of these units via a header attached to the can 20. Furthermore, the can 20 also contains a control unit 18 arranged for receiving and processing sensing information from the sensing circuitry 14, and for controlling the pacing pulse generator 12 and the high energy pulse generator 16, thereby also controlling the timing and delivery of pacing pulses, cardioversion shocks and defibrillation shocks to the heart.

For the purposes of the present invention, use can be made of sensing circuitry, pulse generators and defibrillation and cardioversion units that are known. Since the outlines and functions of such elements are familiar to those skilled in the art, they need not be described in further detail herein.

In FIG. 3, there is shown an alternative embodiment of the present invention. According to this embodiment, the ICD system also has an atrial lead 22, which has a similar configuration as the ventricular lead 24 described above. Thus, the atrial lead 25 also has a tip electrode and a ring electrode spaced apart from the tip electrode. The tip electrode of the atrial lead 22 is positioned in the atrium of the heart 1, as is schematically depicted in FIG. 3.

Furthermore, as is the case with the ventricular lead 24, the atrial lead 22 is also connected to the pacing, sensing and high energy units via the header of the ICD 10, and the sensing circuitry 12 senses atrial capture, the pacing pulse generator 14 delivers atrial pacing pulses, and the high energy pulse generator 16 delivers atrial defibrillation or cardioversion shocks.

Turning now to FIG. 4, the function of the ICD will be described, in particular in relation to the embodiment of the present invention as shown in FIGS. 1 and 2, i.e. with a ventricular lead only. It should be noted, however, that the present invention is equally applicable to the embodiment of FIG. 3.

First, at step 100, the ICD is in its normal mode of operation, namely the autocapture mode. In this mode, the ICU is arranged to perform automatic capture threshold determinations, e.g. in accordance with the AutoCapture™ Pacing System. In this operating mode, capture is verified based on detection of the evoked response (ER) by the sensing circuitry 14 after each single delivered pacing stimulus.

If an evoked response is detected, capture is verified. Failure to detect an evoked response is interpreted as a loss of capture, and a higher energy pacing pulse is delivered as a back-up. If this is immediately followed by another failure to detect an evoked response, then a threshold search is performed. If the threshold search indicates an increase in the capture threshold, then the control unit 18 adjusts the pacing pulse settings by increasing the amplitude for subsequent pacing pulses. Again, a back-up pulse of higher energy is delivered to compensate for the pacing pulse that did not effect any evoked response.

If, for a longer period of time, there are no consecutive failures to detect an evoked response, then a threshold search will be performed every eight hours.

In step 102, a defibrillation shock is delivered in order to terminate ventricular tachycardia and/or fibrillation. This step is of course preceded by the detection of ventricular tachycardia or fibrillation. However, for the purposes of the present invention, use can be made of means and measures well known to the person skilled in the art for detecting tachycardia and/or fibrillation. Thus, a detailed description thereof is not required for the understanding of the present invention and is therefore not needed herein.

Following the delivery of the defibrillation shock, the sensing circuitry 14 checks, at step 104, whether the heart resumes its natural sinus rhythm. When sinus rhythm has been confirmed, at step 106, the control unit 18 switches, at step 110, the mode of operation for the ICD 10 from the autocapture mode to a post-shock mode of operation. The post-shock mode is maintained during a pre-programmed time interval, below referred to as post-shock duration PSD. The time count is reset at step 108 immediately prior to the entry into the post-shock mode.

If it is determined at step 106 that no sinus rhythm is present and that fibrillation still occurs, then the ICD 10 delivers further defibrillation shocks until the defibrillation is successful. For simplifying the description, this has not been illustrated in FIG. 4, but is readily understood by those skilled in the art.

In the post-shock mode, the parameter settings for the pacing pulses delivered by the ICD 10 are adjusted by the control unit 18 to predetermined values. In one example of a preferred embodiment of the invention, the pacing pulse width is adjusted to a predetermined value in the range of 0.5-1.5 ms, and the pacing pulse amplitude is adjusted to a predetermined value in the range of 2.5-7.5 V.

The predetermined pacing pulse parameters may be adapted to the characteristics of the heart of the particular patient in which the ICD is implanted. Furthermore, the parameters for the predetermined pacing pulse settings may also be adjusted after implantation of the ICD, e.g. by a physician during regular follow-ups, in adaptation to physiological changes in the patient.

The post-shock duration is in FIG. 4 denoted as PSD. In this embodiment, the initial post-shock duration is in the range of 5-10 minutes. However, both longer and shorter intervals are conceivable. At step 112, it is determined whether post-shock duration has expired. If this is the case, the sensing circuitry 14 measures one or more selected characteristics of the heart signal, in this case the amplitude of the evoked response or the intrinsic heart beat. However, other characteristics may also be contemplated. The measurement is performed in order to determine whether the myocardium still suffers the effects of the delivered high energy defibrillation pulse to an extent that renders the autocapture mode of operation unsuitable.

Then, the control unit 18 evaluates the measured parameter of the heart signal, here the amplitude $V_{ER}$ of the evoked response signal, and determines, at step 116, whether the amplitude $V_{ER}$ exceeds a predetermined threshold value $V_{ER\_min}$, which is an indication that the evoked response signal is no longer affected by the effects of the delivered shock. If so, the control unit switches, at step 120, the ICD back to the autocapture mode and the normal operation of the ICD is resumed.

However, if the amplitude $V_{ER}$ does not exceed the threshold value $V_{ER\_min}$, i.e. the evoked response signal is still affected by the shock and the cardiac tissue has not yet recovered from the effects of the delivered shock, then the post-shock duration PSD is at step 118 extended by a predetermined time interval. The algorithm is then returned to the loop of steps 1 10 and 112 until the expiry of the extended post-shock duration. Following the expiry thereof, the amplitude $V_{ER}$ is once again measured to determine whether the ICD can be switched back to the autocapture mode. In the illustrated embodiment, this is repeated until the amplitude $V_{ER}$ exceeds the threshold value $V_{ER\_min}$.

In another example, not shown, the amplitude $V_{ER}$ may alternatively or additionally be compared with a highest threshold value. Then, the ICD is switched back to the autocapture mode when the amplitude $V_{ER}$ no longer exceeds the highest threshold value.

Furthermore, the ICD in one embodiment is provided with a maximum post-shock duration limit, or a limit of the number of times that the post-shock duration may be extended. Then, the ICD may switch to the post-shock mode permanently, or to another mode of operation adapted to the case where the heart signal amplitude is permanently increased. The ICD may then be re-programmed by a physician during the next follow-up.

According to the illustrated embodiment, the PSD is extended with the same time interval as the initial post-shock duration, i.e. in the range of 5-10 minutes. However, for other embodiments of the present invention, the extension of the PSD may be selected to be longer or shorter. For still further embodiments, the extension of the PSD may be varied, depending on whether the post-shock duration is extended for the first, second, or third time, etc.

According to yet another embodiment, the predetermined post-shock duration is fixed. In this embodiment, the control unit 18 switches the ICD 10 back to the autocapture mode immediately following the check of the expiry of the post-shock duration at step 112, i.e. steps 114 and 116 are omitted. According to this embodiment, the fixed post-shock duration PSD is in the range of 5-15 minutes, preferably approximately 10 minutes.

According to further embodiments of the invention, and with reference to FIG. 3, the ICD is also arranged for delivering atrial pacing pulses to the atrium of a human heart. As readily understood by the person skilled in the art, the description above with reference to FIG. 4 is equally applicable to the embodiment shown in FIG. 3, regardless of whether it is ventricular or atrial fibrillation that is to be terminated. Thus, following the delivery of a defibrillation shock, the control unit switches the ICD from an autocapture mode to a post-shock mode of operation, in which the atrial pacing pulse settings are adjusted to predetermined pacing pulse parameter values.

In this embodiment, the atrial pacing pulse settings, i.e. pacing pulse width and amplitude, equals that of the ventricular pacing pulse settings described above. Thus, the pacing pulse width is adjusted to a specific predetermined value in the range of 0.5-1.5 ms, and the pacing pulse amplitude is adjusted to a specific predetermined value in the range of 2.5-7.5 V. Furthermore, the criteria for reverting from the post-shock mode to the autocapture mode are the same as described above with particular reference to FIGS. 1, 2 and 4. In this respect, it must however be noted that the predetermined atrial pacing pulse settings could differ from the predetermined ventricular pacing pulse settings.

As readily understood by those skilled in the field, the above described arrangement for terminating ventricular tachycardia and/or fibrillation, as well as the arrangement for terminating atrial tachycardia and/or fibrillation, may be included in a single ICD, such as the ICD described with reference to FIG. 3.

In another embodiment of the present invention, the ICD 10 is provided with an atrial lead 22 only, i.e. there is no ventricular lead. Thus, the ICD 10 is only capable of pacing, sensing and terminating fibrillation or flutter in the atrium of the heart. In a still further embodiment, the ICD 10 has an atrial lead for pacing and terminating fibrillation or flutter in the atrium, but is also provided with a ventricular lead for sensing in the ventricle of the heart. However, it must be noted that since the present invention is not restricted to ventricular pacing or fibrillation, the detailed description above of preferred embodiments for carrying out the present invention applies equally to these two embodiments.

Although modifications and changes may be suggested by those skilled in the art, it is the invention of the inventors to embody within the patent warranted heron all changes and modifications as reasonably and properly come within the scope of their contribution to the art.

We claim as our invention:

1. An implantable cardiac stimulator comprising:
   a pacing pulse generator configured to deliver pacing pulses to at least one chamber of a heart;
   a high energy pulse generator configured to deliver at least one shock selected from the group consisting of cardioversion shocks and defibrillation shocks to at least one chamber of the heart;
   sensing circuitry configured to interact with the heart to sense intrinsic cardiac activity and cardiac activity resulting from capture following a delivered pacing pulse; and
   a control unit connected to said pacing pulse generator, said high energy pulse generator and said sensing circuitry that normally operates said pacing pulse generator in a first mode, including executing an autocapture mode, and that automatically switches said pacing pulse generator from operating in said first mode to operate in a second mode following delivery of a shock by said high energy pulse generator for a post-shock duration and, in said second mode, said control unit operating said pacing pulse to deliver pacing pulses with fixed settings for said pacing pulses and the control circuit does not operate the pacing pulse generator in the autocapture mode during the post-shock duration; and
   said sensing circuitry also being configured to measure signal characteristics of said intrinsic cardiac activity signal following said shock, and wherein said control unit is configured to switch said pacing pulse generator back to said first mode after said post-shock duration, wherein the post-shock duration is extendable by said control unit, dependent on said characteristics of the sensed intrinsic cardiac activity following said shock, until the control unit determines that resumption of said autocapture mode in said first mode will be unaffected by said delivery of said shock.

2. An implantable cardiac stimulator as claimed in claim 1 wherein said post-shock duration is in a range between one minute and fifteen minutes.

3. An implantable cardiac stimulator as claimed in claim 2 wherein said post-shock duration is in a range between five minutes and ten minutes.

4. An implantable cardiac stimulator as claimed in claim 1 wherein said post-shock duration comprises a predetermined basic time interval, and wherein said sensing circuitry measures said signal characteristics prior to expiration of said basic time interval, and wherein said control unit extends said post-shock duration dependent on said characteristics, prior to said expiration of said basic time interval, by adding an extension time interval onto said basic time interval.

5. An implantable cardiac stimulator as claimed in claim 4 wherein said sensing circuitry continues to measure said characteristics prior to expiration of said extension time interval, and wherein said control unit, prior to said expiration of said extension time interval, adds a further extension time interval onto said extension time interval dependent on said characteristics.

6. An implantable cardiac stimulator as claimed in claim 4 wherein said extension time interval is in a range between five minutes and fifteen minutes.

7. An implantable cardiac stimulator as claimed in claim 6 wherein said extension time interval is approximately ten minutes.

8. An implantable cardiac stimulator as claimed in claim 4 wherein said basic time interval is in a range between one minute and fifteen minutes.

9. An implantable cardiac stimulator as claimed in claim 8 wherein said basic time interval is in a range between five minutes and ten minutes.

10. An implantable cardiac stimulator as claimed in claim 1 wherein said characteristics comprise an amplitude of said cardiac activity signal.

11. An implantable cardiac stimulator as claimed in claim 1 wherein said pacing pulse generator includes a pacing pulse delivery arrangement adapted to deliver said pacing pulses to a ventricle of the heart.

12. An implantable cardiac stimulator as claimed in claim 1 wherein said pacing pulse generator includes a pacing pulse delivery arrangement adapted to deliver said pacing pulses to an atrium of the heart.

13. An implantable cardiac stimulator as claimed in claim 1 wherein said high energy pulse generator includes a delivery arrangement adapted to deliver said shock to a ventricle of the heart.

14. An implantable cardiac stimulator as claimed in claim 1 wherein said high energy pulse generator includes a delivery arrangement adapted to deliver said shock to an atrium of the heart.

* * * * *